(12) United States Patent
Nakamura et al.

(10) Patent No.: US 10,744,234 B2
(45) Date of Patent: Aug. 18, 2020

(54) METHOD FOR PREVENTING POSTOPERATIVE ADHESION OF AN ORGAN IN A WOUND SITE

(71) Applicant: Nipro Corporation, Osaka-shi, Osaka (JP)

(72) Inventors: Yusuke Nakamura, Osaka (JP); Kazuhisa Matsuda, Osaka (JP)

(73) Assignee: NIPRO CORPORATION (JP)

( * ) Notice: Subject to any disclaimer, the term of this patent is extended or adjusted under 35 U.S.C. 154(b) by 0 days.

(21) Appl. No.: 15/715,210

(22) Filed: Sep. 26, 2017

(65) Prior Publication Data

US 2018/0015208 A1 Jan. 18, 2018

Related U.S. Application Data

(62) Division of application No. 14/419,260, filed as application No. PCT/JP2013/069921 on Jul. 23, 2013, now abandoned.

(30) Foreign Application Priority Data

Aug. 16, 2012 (JP) .................................. 2012-180332

(51) Int. Cl.
*A61L 31/06* (2006.01)
*A61L 31/14* (2006.01)
*A61L 31/04* (2006.01)

(52) U.S. Cl.
CPC ............ *A61L 31/06* (2013.01); *A61L 31/047* (2013.01); *A61L 31/14* (2013.01); *A61L 31/145* (2013.01); *A61L 2300/424* (2013.01); *A61L 2400/06* (2013.01)

(58) Field of Classification Search
CPC ........................ A61L 2300/424; A61L 2400/06
See application file for complete search history.

(56) References Cited

U.S. PATENT DOCUMENTS

| 7,955,789 B2 | 6/2011 | Izumi et al. |
| 2008/0118907 A1 | 5/2008 | Izumi |
| 2009/0099263 A1* | 4/2009 | Izumi ................... A61K 31/785 514/574 |
| 2010/0260819 A1 | 10/2010 | Obayan |

FOREIGN PATENT DOCUMENTS

| JP | 07310021 | * 11/1995 |
| JP | 92926039 A | 11/1997 |
| JP | 11276572 A | 10/1999 |
| JP | 2009504576 A | 2/2009 |
| WO | 2006054624 A1 | 5/2006 |
| WO | 2007132785 A1 | 11/2007 |

OTHER PUBLICATIONS

Tsao et al (Evaluation of chitosan/γ-poly(glutamic acid) polyelectrolyte complex for wound dressing materials, Carbohydrate polymers, vol. 84, Issue 2, pp. 812-819), Mar. 2011.*
Ho et al., "Polyglutamic Acid Produced by Bacillus subtilis (natto): Structural characteristics, Chemical Properties and Biological Functionalities", Journal of the Chinese Chemical Society, 2006, 53, 1363-1384.
Goto, Atsuo and Masao Kunioka, Biosynthesis and Hydrolysis of Poly(γ-glutamic acid) from Bacillus subtilis IFO3335, Biosci. Biotech. Biochem., 56(7), 1031-1035, 1992.
Tsao et al., "Evaluation of chitosan/γ-poly(glutamic acid) polyelectrolyte complex for wound dressing materials", Carbohydrate polymers, vol. 84, Issue 2, Mar. 2011, pp. 812-819.
Guan-Huei Ho et al., Journal of the Chinese Chemical Society, 2006, vol. 53, No. 6, pp. 1363-1384.

\* cited by examiner

*Primary Examiner* — Gregory Listvoyb
(74) *Attorney, Agent, or Firm* — The Webb Law Firm

(57) ABSTRACT

Provided is a method for preventing postoperative adhesion of an organ in a wound site using the application of an antiadhesive material thereto. The antiadhesive material contains a poly-γ-glutamic acid having a weight-average molecular weight of 600,000 to 13,000,000, or a kinematic viscosity at 37° C. of 2 cSt to 15 cSt when dissolved in distilled water at a concentration of 0.05% by mass and/or a salt thereof, as an effective ingredient. The antiadhesive material may be in a form such as powder, and therefore, for example, is easy to handle even in relatively localized surgery such as endoscopic surgery and can more reliably prevent adhesion.

3 Claims, No Drawings

METHOD FOR PREVENTING POSTOPERATIVE ADHESION OF AN ORGAN IN A WOUND SITE

CROSS-REFERENCE TO RELATED APPLICATIONS

This application is a divisional of co-pending U.S. patent application Ser. No. 14/419,260 filed Jul. 23, 2013, which was the United States national phase of International Application No. PCT/JP2013/069921 filed Jul. 23, 2013, which claims priority to Japanese Patent Application No. 2012-180332 filed Aug. 16, 2012, the disclosures of which are hereby incorporated in their entirety by reference.

TECHNICAL FIELD

The present invention relates to a method of using an antiadhesive material, and more particularly relates to a method of using an antiadhesive material that provides high safety and favorable handleability on the surgery.

BACKGROUND ART

It is known that the surfaces of organs after being damaged during surgery are conjugated to surrounding tissues, and thus postoperative adhesions occur. The postoperative adhesions cause, for example, infertility due to fallopian tube adhesions, intestinal obstruction due to intestinal adhesions, and the like, and require a second surgery, which imposes a heavy burden on patients. Furthermore, the second surgery may even cause additional damage to the organs as a result of dissection of the adhesion site. In order to prevent such postoperative adhesions, an antiadhesive material in film form is known with which a wound site is physically covered on the surgery.

Meanwhile, the cases of endoscopic surgery has recently been increasing because of the small wounds and the relatively short-term hospitalization.

However, in such endoscopic surgery, the use of a conventional antiadhesive material in film form is often difficult. When using an antiadhesive material in film form in endoscopic surgery, it is necessary to roll up the film to a size equal to or smaller than the inner diameter of a trocar, insert the film into the body, open the film in the body, and place the film on an affected part. Thus, the operations are complicated. Therefore, there are cases where the film may be broken, or where the film cannot be correctly placed on the affected part.

In contrast, for example, new antiadhesive materials containing crosslinked poly-γ-glutamic acid as the main ingredient have been developed that can be processed into powder or gel form and are thus easy to handle, see: WO 2006/054624 and WO 2007/132785. However, there are still problems in manufacturing, such as the control of the degree of crosslinking, with these antiadhesive materials.

The present invention has been made to solve the above-described problems, and it is an object thereof to provide an antiadhesive material that is easy to handle even when applied to a case such as endoscopic surgery and that can effectively prevent postoperative adhesion of organs in a wound site.

SUMMARY OF THE INVENTION

The present invention provides a method of using an antiadhesive material containing a poly-γ-glutamic acid having a weight-average molecular weight of 600,000 to 13,000,000 and/or a salt thereof as an effective ingredient.

In one embodiment, the poly-γ-glutamic acid and/or a salt thereof has a kinematic viscosity at 37° C. of 2 cSt to 15 cSt when dissolved in distilled water at a concentration of 0.05% by mass.

In one embodiment, the antiadhesive material is processed into powder or gel form.

In one embodiment, the antiadhesive material is used to prevent postoperative adhesion of an organ in a wound site.

The present invention also provides an antiadhesive material containing a poly-γ-glutamic acid having a kinematic viscosity at 37° C. of 2 cSt to 15 cSt when dissolved in distilled water at a concentration of 0.05% by mass and/or a salt thereof as an effective ingredient.

In one embodiment, the poly-γ-glutamic acid has a weight-average molecular weight of 600,000 to 13,000,000 and/or a salt thereof.

In one embodiment, the antiadhesive material is processed into powder or gel form.

In one embodiment, the antiadhesive material is used to prevent postoperative adhesion of an organ in a wound site.

According to the present invention, it is possible to provide an antiadhesive material that can effectively prevent postoperative adhesion of organs in a wound site and that is easy to handle even in relatively localized surgery such as endoscopic surgery. Moreover, the antiadhesive material and method of the present invention does not essentially require the use of ingredients derived from living organisms, and therefore confirmation of the safety in relation to contamination with infectious agents as strictly required for formulations derived from living organisms is not necessary. Furthermore, there is no need for crosslinking treatment, and it is therefore possible to solve the problems in manufacturing, such as the control of the degree of crosslinking.

DETAILED DESCRIPTION OF THE INVENTION AND BEST MODE

An antiadhesive material used in the present invention contains poly-γ-glutamic acid and/or a salt thereof as an effective ingredient.

In the present invention, poly-γ-glutamic acid is a linear polymer of glutamic acid bound by peptide linkages between γ-carboxyl and α-amino groups. An example of the salt of poly-γ-glutamic acid is sodium poly-γ-glutamate. The poly-γ-glutamic acid and/or a salt thereof that is used in the present invention is uncrosslinked.

The poly-γ-glutamic acid and/or a salt thereof in the present invention has a weight-average molecular weight of, for example, 600,000 to 13,000,000, preferably 800,000 to 10,000,000. If the weight-average molecular weight of the poly-γ-glutamic acid and/or a salt thereof is less than 600,000, even when the material is applied to an affected part of a subject in order to prevent adhesion, the material may not appropriately stay in that affected part due to insufficient viscosity and thus allow the progression of adhesion between the surface of an organ and surrounding tissues without sufficiently exercising appropriate physical barrier functions for the affected part. There is no particular limitation on the upper limit of the weight-average molecular weight, but it is considered that a poly-γ-glutamic acid having a molecular weight exceeding 13,000,000 and/or a salt thereof would be difficult to manufacture using a conventionally known method of manufacturing.

Alternatively, the poly-γ-glutamic acid and/or a salt thereof in the present invention is a polymer having a kinematic viscosity at 37° C. of, for example, 2 cSt to 15 cSt and preferably 2.5 cSt to 8 cSt when dissolved in distilled water at a concentration of 0.05% by mass. If the kinematic viscosity of the poly-γ-glutamic acid and/or a salt thereof is less than 2 cSt, even when the material is applied to an affected part of a subject in order to prevent adhesion, the material may not stay in that affected part due to insufficient viscosity and thus allow the progression of adhesion between the surface of an organ and surrounding tissues without sufficiently exercising appropriate physical barrier functions for the affected part. There is no particular limitation on the upper limit of the kinematic viscosity, but it is considered that a poly-γ-glutamic acid having a kinematic viscosity exceeding 15 cSt and/or a salt thereof would be difficult to manufacture using a conventionally known method of manufacturing.

In the antiadhesive material used in the present invention, the poly-γ-glutamic acid and/or a salt thereof, which is contained as the effective ingredient, satisfies either of the above-described range of weight-average molecular weight or the above-described range of kinematic viscosity under the predetermined conditions, or both.

Examples of the poly-γ-glutamic acid and a salt thereof as described above include those conventionally designated as food additives. Therefore, the safety for living organisms including human bodies has already been ensured.

The poly-γ-glutamic acid or a salt thereof satisfying either of the above-described predetermined range of weight-average molecular weight or the predetermined range of kinematic viscosity, or both that composes the antiadhesive material of the present invention can be easily produced by a person skilled in the art from, for example, a *Bacillus* microorganism such as *Bacillus subtilis* by using, for example, a method described in Biosci. Biotech., 56, 1031-1035 (1992).

The antiadhesive material in the present invention may also contain other ingredient that is effective in preventing adhesion, other ingredient that is effective in retaining a given form, a molecularly targeted drug that targets for a molecule related to adhesion formation, and the like without interfering with the adhesion preventing ability that the poly-γ-glutamic acid or a salt thereof itself has. Examples of the other ingredient that is effective in preventing adhesion include, but not limited to, commonly-used polysaccharides such as amylose, amylopectin, inulin, dextran, dextrin, pectin, alginic acid, carboxymethyl cellulose, and the like; glycosaminoglycans such as hyaluronic acid, alginic acid, heparan sulfate, chondroitin sulfate, chondroitin, dermatan sulfate, keratosulfate, heparin, and the like; disaccharides such as trehalose and the like; alcohols such as glycerin and the like; and synthetic polymers such as polyethylene glycol and the like.

The form of the antiadhesive material in the present invention is not particularly limited, but may be a powder or a gel for the reasons that postoperative adhesion of organs in a wound site can be effectively prevented and that handling is easy even in an area of relatively localized surgery such as endoscopic surgery. In the case of a powder, for example, a poly-γ-glutamic acid and/or a salt thereof that is originally in powder form can be used as it is. In the case of a gel, a poly-γ-glutamic acid and/or a salt thereof that is originally in gel form can be selected and used as it is, or a poly-γ-glutamic acid and/or a salt thereof in powder form can be used after appropriate mixing with a biocompatible medium such as water, saline, or the like and processing into a gel form. When processing into a gel form, it is desirable that a person skilled in the art pays attention to the amount of medium that is used so as not to significantly increase the fluidity of the resultant antiadhesive material. The reason for this is that if the antiadhesive material processed into a gel form has excessively high fluidity, even when the antiadhesive material is applied to an affected part of a subject in order to prevent adhesion, the antiadhesive material may not stay in the affected part due to insufficient viscosity and thus allow the progression of adhesion between the surface of an organ and surrounding tissues without sufficiently exercising appropriate physical barrier functions for the affected part.

The antiadhesive material used in the present invention can be applied on the surgery by, for example, coating or spraying onto a wound site and the surfaces of organs located around the wound site or surrounding tissues. The application may be performed with a plurality of times coating or spraying onto a local portion of the surface of the target organ or surrounding tissues, or with coating or spraying onto the entire target surface at one time. Also, a coating or spraying device may be used. The dose can be appropriately selected by a person skilled in the art.

The antiadhesive material used in the present invention can be applied, without limitation, to organs of humans and other mammals (e.g., laboratory animals, pets, or domestic animals, such as mice, rats, hamsters, rabbits, dogs, cats, cattle, swine, sheep, deer, wild boars, and the like). Specific examples of the organs include digestive organs (stomach, small intestine, large intestine, and the like), genital organs (uterus, ovary, or the like), circulatory organs (heart, blood vessels, lymphatic vessels, and the like), respiratory organs (e.g., lung), locomotive organs (muscles, bones, ligaments, and the like), and sensory organs (eyeballs and the like).

The antiadhesive material in the present invention can be effectively used in not only endoscopic surgery but also common surgery.

EXAMPLES

Hereinafter, the present invention will be more specifically described by means of examples. However, the present invention is not limited by the examples below.

Weight-Average Molecular Weight and Kinematic Viscosity

With respect to the weight-average molecular weights (excluding catalog values) and kinematic viscosities shown in the following examples and comparative examples, these properties of samples were measured as described below and thus confirmed before the samples were used.

(1) Measurement of Weight-Average Molecular Weight

سodium poly-γ-glutamate dissolved in distilled water was subjected to gel permeation chromatography under the following conditions, and the weight-average molecular weight was measured.

Column: Shodex Asahipak GF-710HQ (manufactured by Showa Denko K.K.)
Column temperature: 40° C.
Mobile phase: 50 mM sodium chloride aqueous solution
Flow rate: 0.6 mL/minute
Injected amount: 100 μL
Detector: UV 220 nm Note that pullulan was used as the reference material.

(2) Measurement of Kinematic Viscosity

With respect to sodium poly-γ-glutamate dissolved in distilled water (concentration of 0.05% w/w), the kinematic viscosity (cSt) was measured using an Ubbelohde viscometer (manufactured by Sibata Scientific Technology Ltd., (model) SU-00286) at a sample temperature of 37° C. The kinematic viscosity was calculated by the following equation using the obtained efflux time (sec):

"Kinematic viscosity (cSt)=Constant of the viscometer×Efflux time (sec)".

Examples 1 and 2 and Comparative Examples 1 to 3: Confirmation of Adhesion Preventing Effect Donryu rats (male, 5 to 8 weeks old) were divided into five groups, namely, Groups A, B, C, D, and E such that each group was composed of 4 to 8 rats. Each rat was subjected to laparotomy by abdominal midline incision under general anesthesia. The ileocecum of the large intestine was taken out of the abdominal cavity. The serosal surface thereof was rubbed with gauze until small bleeding spots appeared, and then exposed to warm air from a dryer for about 10 seconds. Subsequently, an about 1 cm×1 cm area of the abdominal wall directly above the ileocecum of the the large intestine was excised, and the abdominal wall was exposed to warm air from a dryer for about 10 seconds, and then dried in room air for about 10 minutes.

Then, with respect to the rats in Group A, the rubbed portion of the ileocecum and the excision portion of the abdominal wall were coated with about 0.2 g of a sodium poly-γ-glutamate powder having a weight-average molecular weight of 1,100,000 to 1,300,000 and a kinematic viscosity of 3.2 cSt to 3.5 cSt (PGA; Example 1) such that the entire surface of those portions was covered, and the abdomen was closed such that the rubbed portion of the ileocecum and the excision portion of the abdominal wall came into contact with each other.

With respect to the rats in Group B, the rubbed portion of the ileocecum and the excision portion of the abdominal wall were coated with about 0.2 g of a sodium poly-γ-glutamate powder having a weight-average molecular weight of 9,800,000 and a kinematic viscosity of 7.7 cSt (PGA; Example 2) such that the entire surface of those portions was covered, and the abdomen was closed such that the rubbed portion of the ileocecum and the excision portion of the abdominal wall came into contact with each other.

With respect to the rats in Group C, the rubbed portion of the ileocecum and the excision portion of the abdominal wall were coated with about 0.2 g of a crosslinked poly-γ-glutamic acid obtained by crosslinking poly-γ-glutamic acid by gamma-irradiation (crosslinked PGA; Comparative Example 1) such that the entire surface of those portions was covered, and the abdomen was closed such that the rubbed portion of the ileocecum and the excision portion of the abdominal wall came into contact with each other.

With respect to the rats in Group D, a sheet of Seprafilm (manufactured by Kaken Pharmaceutical Co., Ltd.; Comparative Example 2) was placed on each of the rubbed portion of the ileocecum and the excision portion of the abdominal wall so as to cover the corresponding portion, and the abdomen was closed such that the rubbed portion of the ileocecum and the excision portion of the abdominal wall came into contact with each other.

With respect to the rats in Group E, no further treatment was performed (Comparative Example 3), and the abdomen was closed such that the rubbed portion of the ileocecum and the excision portion of the abdominal wall came into contact with each other.

One week later, the rats in Groups A to E were subjected to laparotomy again, and with respect to each group, the extent of adhesion in the rubbed portion of the ileocecum and the excision portion of the abdominal wall was visually observed, graded according to the following six-level adhesion scores, and evaluated. The results are shown in Table 1.

Adhesion Scores:

0, no adhesion;

1, mild adhesion separatable by blunt dissection was observed;

2, adhesion requiring sharp dissection was observed at a rate of 50% or less;

3, adhesion requiring sharp dissection was observed at a rate of 50% or more;

4, the serosa of the cecum was damaged during dissection; and 5, the full-thickness of the cecum was damaged during dissection.

TABLE 1

|  | Example 1 Group A (PGA) | Example 2 Group B (PGA) | Comparative Example 1 Group C (Crosslinked PGA) | Comparative Example 2 Group D (Seprafilm) | Comparative Example 3 Group E (No treatment) |
|---|---|---|---|---|---|
| Score: 0 | 4 | 1 | 1 | 0 | 0 |
| Score: 1 | 0 | 3 | 5 | 0 | 0 |
| Score: 2 | 0 | 0 | 2 | 1 | 0 |
| Score: 3 | 2 | 0 | 0 | 3 | 0 |
| Score: 4 | 0 | 0 | 0 | 1 | 3 |
| Score: 5 | 0 | 0 | 0 | 1 | 2 |
| Average Value | 1.0 ± 1.5 | 0.8 ± 0.5 | 1.1 ± 0.6 | 3.3 ± 1.0 | 4.4 ± 0.5 |

Numerical values in the table show the number of individuals.

As shown in Table 1, it is found that the sodium poly-γ-glutamates used in Examples 1 and 2 achieved excellent adhesion scores that are equivalent to that of Comparative Example 1. When compared with the sodium poly-γ-glutamates of Examples 1 and 2, the conventional film formulation of Comparative Example 2 or the non-treated state of Comparative Example 3 has a tendency toward higher adhesion scores, and thus it is found that the antiadhesive material of the present invention could effectively prevent postoperative adhesion of the organs in the wound site.

Comparative Example 4 and Examples 3 and 4: Comparison of Localization Effect in Virtual Affected Part Three polystyrene (PSt) Petri dishes were prepared. Then, 20 mg each of a sodium poly-γ-glutamate powder having a weight-average molecular weight of 800,000 and a kinematic viscosity of 2.8 cSt (Example 3), a sodium poly-γ-glutamate powder having a weight-average molecular weight of 1,500,000 to 2,500,000 (catalog value) and a kinematic viscosity of 5.5 cSt (manufactured by Wako Pure Chemical Industries, Ltd.; Example 4), and a sodium poly-γ-glutamate powder having a weight-average molecular weight of 200,000 to 500,000 (catalog value) and a kinematic viscosity of 1.1 cSt (manufactured by Wako Pure Chemical Industries, Ltd.; Comparative Example 4) were applied to the respective Petri dishes by coating. After that, 0.1 ml of distilled water was added to each Petri dish and mixed using a spatula to form a gel.

Then, the PSt Petri dish was tilted at about 45 degrees, and the fluidity of the gel on the bottom surface of the Petri dish was checked. The obtained results are shown in Table 2.

TABLE 2

| | Weight-Average Molecular Weight | Kinematic Viscosity | Fludity |
|---|---|---|---|
| Comparative Example 4 | 200,000 to 500,000 (catalog value) | 1.1 cSt | Observed |
| Example 3 | 800,000 | 2.8 cSt | Not observed |
| Example 4 | 1,500,000 to 2,500,00 (catalog value) | 5.5 cSt | Not observed |

As shown in Table 2, the sodium poly-γ-glutamate powder of Comparative Example 4, as having a weight-average molecular weight of less than 600,000 or a kinematic viscosity of less than 2 cSt, exhibited increased fluidity when gelled, and readily flowed when the Petri dish was tilted. In contrast, the sodium poly-γ-glutamate powders of Examples 3 and 4 having a weight-average molecular weight or a kinematic viscosity exceeding these ranges had a tendency of the gel to be likely to stay in place on the bottom surface of the Petri dish. Thus, it is found that the antiadhesive material of the present invention after being applied to an affected part of a subject has a tendency to stay in that affected part even when swelled with, for example, moisture etc. in the body of the subject and gelled, and thus can prevent the progression of adhesion between the surface of an organ and surrounding tissues by exercising appropriate physical barrier functions for the affected part.

According to the present invention, it is possible to effectively prevent postoperative adhesion of organs in a wound site. The antiadhesive material used in the present invention may have any form such as powder or gel form, and therefore, for example, is easy to handle even in relatively localized surgery such as endoscopic surgery and can more reliably prevent adhesion.

The invention claimed is:

1. A method for preventing postoperative adhesion of an organ in a wound site comprising:
    applying powder form of a sodium poly-γ-glutamate as a sole component to the wound site of a subject as it is, wherein the sodium poly-γ-glutamate is substantially uncrosslinked and is processed into powder form, and wherein applying the powder form of the sodium poly-γ-glutamate comprises spraying the powdered sodium poly-γ-glutamate onto the wound site or to surrounding tissue.

2. The method of claim 1, wherein the sodium poly-γ-glutamate has a weight-average molecular weight of 600,000 to 13,000,000.

3. The method of claim 1, wherein the organ is digestive organ, genital organ, circulatory organ, respiratory organ, locomotive organ or sensory organ.

* * * * *